(12) United States Patent
Zantl et al.

(10) Patent No.: US 9,927,421 B2
(45) Date of Patent: Mar. 27, 2018

(54) SAMPLE CHAMBER

(75) Inventors: Roman Zantl, Baldham (DE); Valentin Kahl, München (DE)

(73) Assignee: IBIDI GMBH, Martinsried (DE)

( * ) Notice: Subject to any disclaimer, the term of this patent is extended or adjusted under 35 U.S.C. 154(b) by 1252 days.

(21) Appl. No.: 12/565,595

(22) Filed: Sep. 23, 2009

(65) Prior Publication Data
US 2010/0081189 A1    Apr. 1, 2010

(30) Foreign Application Priority Data
Sep. 30, 2008    (EP) .................................... 08017224

(51) Int. Cl.
*B01L 1/00* (2006.01)
*B01L 3/00* (2006.01)
*G01N 33/483* (2006.01)

(52) U.S. Cl.
CPC .... *G01N 33/4836* (2013.01); *B01L 3/502715* (2013.01); *B01L 2200/027* (2013.01); *B01L 2200/10* (2013.01); *B01L 2300/0645* (2013.01); *B01L 2300/0829* (2013.01)

(58) Field of Classification Search
CPC .............. B01L 3/5027; B01L 3/502715; B01L 2300/041; B01L 2300/0645; B01L 2200/025
USPC ............... 204/400, 403.01, 412, 450, 451; 422/82.01; 435/6.13, 7.93, 285.2, 435/287.1–287.2, 288.5–288.7, 288.3, 435/288.4; 240/403.01–403.04
See application file for complete search history.

(56) References Cited

U.S. PATENT DOCUMENTS

| | | | | |
|---|---|---|---|---|
| 4,115,230 A | * | 9/1978 | Beckman ...................... | 204/431 |
| 4,505,807 A | * | 3/1985 | Yamada ........................ | 204/425 |
| 5,187,096 A | * | 2/1993 | Giaever et al. ............ | 435/287.1 |
| 5,563,067 A | * | 10/1996 | Sugihara ................ | C12M 41/46 |
| | | | | 204/403.01 |
| 6,544,734 B1 | | 4/2003 | Briscoe et al. | |
| 6,749,740 B2 | * | 6/2004 | Liamos et al. ................ | 205/792 |
| 6,817,738 B1 | * | 11/2004 | Winters et al. ............... | 362/368 |
| 6,866,758 B2 | * | 3/2005 | Bhullar et al. ........... | 204/403.02 |

(Continued)

FOREIGN PATENT DOCUMENTS

DE    10229210 A1    1/2004
WO    03087410 A1    10/2003

(Continued)

*Primary Examiner* — Nathan A Bowers
(74) *Attorney, Agent, or Firm* — Moore & Van Allen PLLC; Henry B. Ward, III (57) ABSTRACT

The invention relates to a sample chamber for testing samples, comprising a bottom plate and a cover plate connected thereto, a sample reservoir for receiving a liquid and/or a sample to be tested, and a contact electrode which is arranged entirely in the bottom plate, in the cover plate or between the bottom plate and the cover plate and which is electrically conductively connected to a conductor element or semiconductor element disposed in and/or on the sample chamber, wherein the bottom plate and/or the cover plate are designed in such a way that an electrical contact with the contact electrode can be established from the outside in such a way that an electrically conductive connection to the conductor element or to the semiconductor element can be established from the outside through the bottom plate or through the cover plate via the contact electrode.

6 Claims, 5 Drawing Sheets

(56) References Cited

U.S. PATENT DOCUMENTS

| | | | |
|---|---|---|---|
| 7,063,776 B2* | 6/2006 | Huang | 204/403.14 |
| 2005/0004442 A1 | 1/2005 | Ozaki et al. | |
| 2005/0196857 A1 | 9/2005 | Lee | |
| 2006/0141612 A1* | 6/2006 | Yamamoto et al. | 435/287.2 |
| 2008/0057570 A1 | 3/2008 | Natarajan et al. | |

FOREIGN PATENT DOCUMENTS

| | | | |
|---|---|---|---|
| WO | 2006097751 A2 | | 9/2006 |
| WO | WO2007/092571 | * | 8/2007 |

* cited by examiner

SAMPLE CHAMBER

FIELD OF THE INVENTION

The invention relates to a sample chamber for testing especially chemical and biological samples, to a sample chamber holder and to a system comprising a sample chamber and a sample chamber holder.

BACKGROUND OF THE INVENTION

Especially in the fields of cytobiology and medicine sample chambers having integrated conductor paths and electrodes are used for the testing of cells, specifically living cells. Among others, the alternating current resistance of an electrode covered with cells is measured as a function of time. Such sample chambers are also referred to as MEA (Multi Electrode Array) systems. Also, it is possible to use MEA systems for chemical and pharmacological applications.

A MEA system is known, for example, from U.S. Pat. No. 5,187,096 which comprises several receiving wells for receiving the cells to be tested, in which electrodes are arranged for measuring the impedance of cell cultures. The electrodes are connected to contact strips which are, again, connected to leads leading out of the MEA system. In order to supply power or connect the contact strips to measuring devices the leads are connected to external equipment.

Another MEA system combined with a holder is known from U.S. Pat. No. 5,563,067. The apparatus comprises a device for receiving cells, which is arranged on a carrier and on the bottom of which a planar electrode with a plurality of microelectrodes is arranged. Again, conductors are led out of the device for receiving the cells. These conductors are arranged on the upper surface of the carrier and comprise several electrical contact points for the connection to a power supply or for connecting the conductors to measuring devices.

In any one of these systems electrical contact points serve to establish an electrically conductive connection to conductors in the MEA system. Again, measuring electrodes inside a device for receiving cells are connected to the conductors. An external voltage source or a suitable measuring device can be connected to the contact points, specifically by means of contact elements on the holder of the MEA system.

All of the prior systems have in common that the contact points project over the device for receiving cells of the MEA system. Especially in systems where the conductors and electrodes are formed of very thin layers or are arranged on thin carrier plates it may occur that the contact points or the conductors connecting same to the electrodes in the MEA system are easily damaged.

BRIEF SUMMARY OF THE INVENTION

Therefore, it is the object of the invention to provide a sample chamber comprising an electrical contact electrode and a conductor path as well as a sample chamber holder to establish an electrical contact, so as to protect the contact electrodes and/or conductor paths against damage.

This object is achieved with a sample chamber according to the claimed invention.

The sample chamber according to the invention for testing samples comprises a bottom plate and a cover plate connected thereto, a sample reservoir for receiving a liquid and/or a sample to be tested, and a contact electrode which is arranged entirely in the bottom plate, in the cover plate or between the bottom plate and the cover plate and which is electrically conductively connected to a conductor element or semiconductor element disposed in and/or on the sample chamber, wherein the bottom plate and/or the cover plate are designed in such a way that an electrical contact with the contact electrode can be established from the outside in such a way that an electrically conductive connection to the conductor element or to the semiconductor element can be established from the outside through the bottom plate or through the cover plate via the contact electrode.

The sample chamber according to the invention permits a safer contacting of the contact electrode. Specifically, the contact electrode is protected against damages since it does not project over the sample chamber. The sample chamber permits to establish a direct, that is, mechanical contact between the contact electrode and an external contact element from the outside, so as to allow a current to be conducted via this contact. Specifically, an electrical contact with the contact electrode can be established from the outside through the bottom plate or through the cover plate.

The sample reservoir of the sample chamber may be formed by a recess or groove in the cover plate and/or the bottom plate. In the case of a groove or recess in the cover plate and/or the bottom plate on the inner side of the sample chamber a sample reservoir in the form of a hollow space is formed, whereby the hollow space may be provided entirely between the cover plate and the bottom plate. Alternatively, the sample chamber may include an outwardly open reservoir. To this end, the bottom plate or the cover plate may have a hole. The hole may be a through-hole. The cover plate may have a through-hole, and the bottom plate may have a recess or groove pointing in the direction of the hole. Alternatively, the bottom plate may have a through-hole, while the cover plate may have a recess or groove pointing in the direction of the hole.

The sample chamber itself may be provided in the most various geometries and shapes. In one of the simplest embodiments the sample chamber comprises a planar bottom plate which is connected to the cover plate. The cover plate may include a recess or groove, wherein a sample reservoir is defined by the recess or groove in the cover plate in connection with the bottom plate. The shape of the sample reservoir can be determined by the geometry of the recess in the cover plate. For example, a sample reservoir in the form of a channel-shaped hollow space may be defined by a longitudinal groove in the cover plate. A sample to be tested and/or a liquid may be introduced into the sample reservoir. The sample chamber may be used for chemical and/or biological tests of chemical and/or biological samples. The samples can be, for example, living cells, proteins, DNA, viruses etc. The sample chamber may also comprise a plurality of sample reservoirs. Specifically, the plurality of sample reservoirs may be connected to each other fluidically. The bottom plate and/or cover plate may be formed of an injection molded part or may be formed by joining a plurality of plastic components. Specifically, the shapes and/or the material of the plurality of plastic components may be different.

Specifically, the conductor element may be designed as a conductor path.

According to a further development the sample chamber may have a hole in which the contact electrode is arranged. Thus, the contact electrode is freely accessible from the outside and can directly be contacted with an external contact element, e.g. a spring-loaded contact pin. Specifically, the contact electrode may be arranged on a side wall of the hole and/or on the bottom of the hole. The hole may be a through-hole in the sample chamber. In the case of a through-hole in the sample chamber the contact electrode is arranged on a side wall. The side from which a contact is made can be freely chosen through the through-hole in the sample chamber.

Alternatively, the hole may be a blind hole in the cover plate or in the bottom plate. This is an advantage if the conductor element or the semiconductor element is arranged at least partially in the bottom plate or in the cover plate. The hole may be a blind hole in the sample chamber. In this case, the blind hole may be formed by a through-hole in the bottom plate and by the cover plate. Alternatively, the blind hole may be formed by through-hole in the cover plate and by the bottom plate. The contact electrode may be arranged on the bottom plate or on the cover plate in such a way that it is arranged at least partially on the bottom of the blind hole. Thus, the sample chamber is easy to produce. Especially if the contact electrode is arranged on the bottom of the blind hole it can be contacted with a simple contact pin, specifically with a spring-loaded contact pin.

The hole may be filled partially or completely with an electrically conductive material. In this way, the contact electrode is arranged entirely in the cover plate or in the bottom plate and is directly accessible from the outside, and an electrical contact with the contact electrode can be established.

Specifically, at least one of the orifices of the hole, especially the outer orifice, may be disposed in a plane which is parallel relative to the base surface of the sample chamber. The base surface of the sample chamber may be the outer surface on which the sample chamber lies during normal operation. Thus, an electrical contact with the contact electrode can be established easily from above or below.

According to a further development the sample chamber may comprise one or more further contact electrodes. Specifically, each of the contact electrodes may be arranged entirely in the bottom plate, in the cover plate or between the bottom plate and the cover plate and be electrically conductively connected to a conductor element or semiconductor element disposed in and/or on the sample chamber. Thus an electrically conductive connection to a plurality of conductor elements and/or semiconductor elements disposed on and/or in the sample chamber can be established by a contact electrode from the outside through the bottom plate or through the cover plate.

Specifically, the sample chamber can include a plurality of holes in each of which one contact electrode is arranged. Alternatively, also several contact electrodes may be arranged in one hole.

Each of the holes may have any of the aforementioned features. The cross-section of the orifice of each of the holes may be smaller, larger than or have the same size as the surface area of the respective contact electrode arranged therein. If several contact electrodes are arranged in one hole the cross-section of the orifice may preferably be larger than the sum of the surface areas of the contact electrodes so as to electrically insulate them from each other.

According to a further development the sample chamber may comprise a measuring electrode and/or excitation electrode each of which is electrically conductively connected to a contact electrode by a conductor element or semiconductor element. Specifically, a measuring electrode and/or excitation electrode may be arranged in a sample reservoir, for example, in form of a hollow space. Measuring electrodes can serve, for example, to measure the impedance of a cell culture in the sample reservoir. Excitation electrodes can serve to apply a voltage to the sample.

Specifically, the contact electrode, the measuring electrode, the excitation electrode and/or the conductor element may include gold, platinum, titanium or TiNi (titanium nickel). In one embodiment the semiconductor element may include ITO (indium-tin-oxide).

Specifically, the semiconductor element may serve the temperature control of the sample chamber.

The conductor element and the contact electrode and/or the measuring electrode and the excitation electrode, respectively, may be made of one material. This simplifies the production of the sample chamber, and the electrical properties of the conductor element and the contact electrode, the measuring electrode and/or the excitation electrode are homogenous. Specifically, the conductor element and the contact electrode may be made of one material.

According to a further development the conductor element, the semiconductor element, the contact electrode, the measuring electrode and/or the excitation electrode may be planar. Especially in view of the contact electrode this can facilitate the establishment of a stable electrical contact from the outside.

The conductor element, the semiconductor element, the measuring electrode and/or the excitation electrode may have a thickness of 10 nm to 5 µm, specifically 10 nm to 300 nm.

According to a further development the contact electrode, the measuring electrode, the excitation electrode, the semiconductor element and/or the conductor element may be disposed on the bottom plate and/or the cover plate, with the contact electrode being arranged entirely between the bottom plate and the cover plate. This has the advantage that the production of the sample chamber is simplified.

Specifically, the conductor element and/or the semiconductor element may be disposed entirely between the bottom plate and the cover plate or entirely on the outer side of the sample chamber or partially between the bottom plate and the cover plate and partially on the outer side of the sample chamber. If the conductor element and/or the semiconductor element are located entirely between the bottom plate and the cover plate, there is the advantage that they are protected against damages.

The conductor element and/or the semiconductor element may be disposed entirely or partially inside the bottom plate and/or cover plate of the sample chamber. Specifically, the measuring electrode and/or the excitation electrode may be arranged partially inside the bottom plate and/or the cover plate of the sample chamber. This is advantageous if only a part of the surface of the measuring electrode and/or the excitation electrode is to come into contact with the sample.

The conductor element, the semiconductor element, the measuring electrode and/or the excitation electrode may be arranged entirely or partially in a sample reservoir and, specifically, may be electrically insulated entirely or partially from the sample reservoir. Specifically, the measuring electrode and/or the excitation electrode may be formed by parts of the conductor element or the semiconductor element which are not or partially insulated from the sample reservoir. Thus, the sample chamber can be produced easily and efficiently. The size of the electrode may be determined by the size of the insulating layer.

In one embodiment the sample chamber may comprise a heating element, specifically one that is connected to the contact electrode in an electrically conductive manner. The heating element may be a part of the sample chamber, that is, it may be integrated in the sample chamber. Specifically, the integrated heating element may be arranged on and/or in the bottom plate and/or the cover plate. Specifically, the heating element may comprise the semiconductor element. For example, the outer side of the sample chamber may entirely or partially comprise the semiconductor element. Specifically, the semiconductor element, especially ITO, may be arranged on and/or in the bottom plate. Thus, a temperature control of the surface of the entire bottom plate can be achieved. Special temperature-dependent resistance elements, e.g. PT100, may be used to determine the temperature and control it by a feedback control system.

According to a further development the cover plate and the bottom plate may directly be connected to each other, specifically surface to surface. Thus, the bottom plate and the cover plate can stabilize each other and protect a contact electrode, specifically one arranged between the bottom plate and the cover plate, against damages. Especially if the bottom plate or the cover plate is thin, e.g. with a thickness of between 1 µm and 300 µm, this is an advantage. Moreover, the sample chamber can be produced more easily and in a more compact manner. Specifically, the cover plate and the bottom plate may be connected to be flush with each other.

Specifically, the cover plate and the bottom plate may be connected to each other in a non-destructively detachable or destructively detachable manner. For example, the cover plate and the bottom plate may be glued or welded together, specifically by means of laser welding, ultrasonic welding, thermal welding or solvent welding.

The cover plate and the bottom plate may be connected to each other in a non-destructively detachable manner, for example, by PDMS bonding. Especially if the conductor element is disposed on the bottom plate and the cover plate it is advantageous if the cover plate and the bottom plate are welded together. The bottom plate and the cover plate may be connected in a liquid-tight manner. Especially solvent welding and thermal welding have the advantage that no liquid is diffused, for example along the conductor elements, if non-insulated conductor elements are used that may be arranged between the bottom plate and the cover plate.

The bottom plate and/or the cover plate may comprise glass, specifically cover glass, or plastic, specifically COC (cyclo-olefine copolymer), COP (cyclo-olefine polymer), PC (polycarbonate), PS (polystyrene), PE (polyethylene) or PMMA (polymethylmethacrylate).

The bottom plate and/or the cover plate may have a predetermined inherent fluorescence, which is specifically smaller than or equal to the inherent fluorescence of COC or COP or a conventional cover glass, and/or a predetermined refraction index, specifically >1.2 and/or <1.7.

Specifically, the inherent fluorescence may be smaller than or equal to the inherent fluorescence of a conventional cover glass (for example, pure white glass of hydrolytic class 1, such as Menzel cover glass, especially of thickness no. 1.5). The predetermined refraction index may specifically be >1.2 and/or <1.7. Such an optically high-quality material advantageously permits the performance of microscopic tests. For example, the double refraction may be so small as to allow DIC (Differential Interference Contrast). A low inherent fluorescence permits the performance of fluorescence measurements.

Specifically, the bottom plate and/or the cover plate may be antireflection-coated in a frequency range of the electromagnetic radiation used for microscopy. Thus, the transmission through the bottom plate and/or the cover plate can be increased so as to allow individual molecule measurements by means of fluorescence. To obtain antireflection, the bottom plate and/or the cover plate may be provided with a coating. For example, an ITO layer may be applied to the bottom plate and/or the cover plate. The thickness of the ITO layer can be chosen to antireflect the bottom plate and/or the cover plate in a frequency range of the electromagnetic radiation used for microscopy. The thickness of the ITO layer can be, for example, $\lambda/2$ to $4\lambda$ so as to obtain antireflection, wherein $\lambda$ specifies the wavelength used. Specifically, the wavelength $\lambda$ may be in the range of 300 nm to 700 nm. In this case, the thickness of the coating may be between 200 nm and 1 µm. Specifically, the ITO layer may also be used for controlling the temperature of the sample chamber.

The bottom plate may at least partially be planar. The planar part of the bottom plate may have a thickness of between 1 µm and 300 µm, specifically between 60 µm and 220 µm. This is an advantage in order to allow a high-resolution microscopy through the bottom plate because, in this case, the working distance of the objective to the sample may be small. It is then possible, for example, to work with high-resolution objectives, e.g. with 63× or 100× or with apertures of 1.2 and greater, respectively.

In one embodiment the cover plate may at least partially be planar, and the planar part of the cover plate may have a thickness of at least 0.5 mm, specifically between 1 mm and 2 mm. This permits a stabilization of the bottom plate connected to the cover plate, especially if the bottom plate is very thin, that is, for example, if it has a thickness between 1 µm and 300 µm.

The bottom plate and/or the cover plate may comprise an orifice for filling the sample reservoir, specifically in the form of a hollow space, with a liquid and/or a sample to be tested, and/or for removing a liquid and/or a sample to be tested.

The sample chamber may comprise one or more further, specifically outwardly open reservoirs. These further reservoirs may each be fluidically connected to one or more sample reservoirs. This permits adding or removing a liquid and/or a sample to and from the sample reservoir. Specifically, two outwardly open reservoirs may be provided on two, specifically opposite sides of a sample reservoir, specifically in the form of a channel-shaped hollow space. This permits a fast exchange of the liquid and/or sample located in the sample reservoir.

Specifically, the bottom plate and/or the cover plate may comprise a connecting element, specifically for connecting the sample chamber to devices for sucking off and/or adding a liquid and/or a sample from and to a sample reservoir and/or a further reservoir of the sample chamber. Specifically, the connecting element may have the shape of a luer adapter. The connecting element of the bottom plate and/or the cover plate may comprise the orifice. Specifically, the connecting element may be fluidically connected to the sample reservoir and/or a further reservoir. Thus, a conical plug connection can be realized, e.g. to the tip of a pipette, for filling or emptying the reservoir or for sealing it in an air-tight and liquid tight manner, specifically by means of a conical plug or other sealing elements. To this end, the orifice and the connecting element may be disposed directly above the sample reservoir, specifically in the form of a hollow space, or above a further reservoir. The connecting element may also be connected via a channel to the sample reservoir and/or a further reservoir. The device for sucking off and/or adding a liquid and/or a sample from and to the sample reservoir or a further reservoir of the sample chamber can be, for example, a pipette or a hose. The connecting element may have a conical shape. Thus, a sealed connection can be established.

According to a further development the sample chamber may be dimensioned in such a way that the volume of the sample reservoir or a further reservoir is in the range of 5 µl to 5000 µl, specifically between 100 µl and 500 µl. Thus, the sample chamber can be utilized for microfluid tests. This is advantageous if small quantities of biological or chemical samples are being worked with or if the microfluid behavior of the sample is to be tested.

The invention further provides a sample chamber holder for holding a sample chamber, wherein the sample chamber comprises a contact electrode which is accessible from the outside, comprising a first frame element and a second frame element, at least one electrical contact element which is disposed on the first or second frame element, a connecting device for connecting the first and second frame element so as to obtain an assembled sample chamber holder with a predetermined relative position of the frame elements with respect to each other, wherein the connecting device comprises at least one magnetic and/or magnetizable element, and wherein the first and the second frame element are designed in such a way that an inventive sample chamber is fixed in the assembled sample chamber holder between the first and the second frame element, and wherein, in the assembled sample chamber holder, the electrical contact element of the sample chamber holder is electrically conductively connected to the contact electrode of the fixed sample chamber.

Specifically, the sample chamber holder may hold one of the above-described sample chambers.

This sample chamber holder allows a safe contacting of a sample chamber. Another advantage of this sample chamber holder is that, owing to the connecting device which comprises at least one magnetic and/or magnetizable element, it may be more compact and smaller than a sample chamber holder whose connecting element comprises, for example, screw elements.

Specifically, the connecting device may comprise at least one or more permanent magnets. Thus, it is not required to screw the two frame elements of the sample chamber together, and the sample chamber holder may be realized so compact and miniaturized to allow its integration in an incubation apparatus. For example, four permanent magnets may be used on each frame element.

According to a further development the first frame element and/or the second frame element may include recesses for receiving the sample chamber. This facilitates a safe positioning and fixing of the sample chamber. Specifically, the correct arrangement of the sample chamber can thus be facilitated for the user.

The electrical contact element of the sample chamber holder may comprise a spring contact. Specifically, the electrical contact element of the sample chamber holder may comprise a spring-loaded contact pin. Thus, a stable electrical contact can be established, for example, with an above-described sample chamber.

According to a further development the first frame element and/or the second frame element may be adapted to allow a microscopical examination of a sample in the sample chamber. This is an advantage if not only the electrical conductive properties of the sample in the sample chamber are to be tested, but also if microscopical examinations are to be carried out.

Specifically, the first frame element and/or the second frame element may include a through-hole or a transparent area, specifically made of glass or plastic. Thus, a microscope lens can be brought near the sample in the sample chamber. The exemplary transparent area of the first and/or second frame element is, for this purpose, at least transparent for the frequency range of the electromagnetic spectrum in which the microscopical examination is to be carried out.

The transparent area in the first frame element and/or in the second frame material may comprise a material that has optical properties as were described above by means of examples for the bottom plate and/or the cover plate of the sample chamber.

According to a further development the sample chamber holder may be temperature-controllable, specifically by an ITO coating. The sample chamber holder may be passively temperature-controllable by detachably connecting it to a temperature-controllable element. Specifically, the sample chamber holder itself may comprise a temperature control element. The sample chamber holder can, for example, be coated entirely or partially with ITO, especially in a transparent part of the first and/or second frame element. Thus, a surface temperature control may be performed. Special temperature-dependent resistance elements, e.g. PT100, may be used to determine the temperature and control it by a feedback control system.

Moreover, the sample chamber holder may comprise a connecting device for electrically contacting the sample chamber holder from the outside. Thus, the sample chamber can be connected via the sample chamber holder to an external device, specifically a voltage source or a measuring device. To this end, the sample chamber holder is contacted via the connecting device. At least one contact element of the sample chamber holder thereupon establishes an electrical contact with the contact electrode of the sample chamber. The connecting device may comprise a plug connection element or a cable. The sample chamber holder may be connected to external devices, e.g. to a voltage source or a measuring device. This connection can be achieved with an electrically conducting cable connection, wherein the cable is electrically conductively connected to the at least one electrical contact element of the sample chamber holder. Alternatively, a plug connection element can also be designed to allow a conductive connection to an external element, e.g. a base plate, wherein this external element, again, may comprise corresponding conductive connections.

The invention further provides a system, comprising a sample chamber as described above and a sample chamber holder as described above.

Such a system allows a safe contacting of an inventive sample chamber, wherein the contact electrodes are protected against damages.

BRIEF DESCRIPTION OF THE DRAWINGS.

Additional features and advantages shall be explained below by means of the exemplary figures.

DETAILED DESCRIPTION OF THE INVENTION

Figure 1:
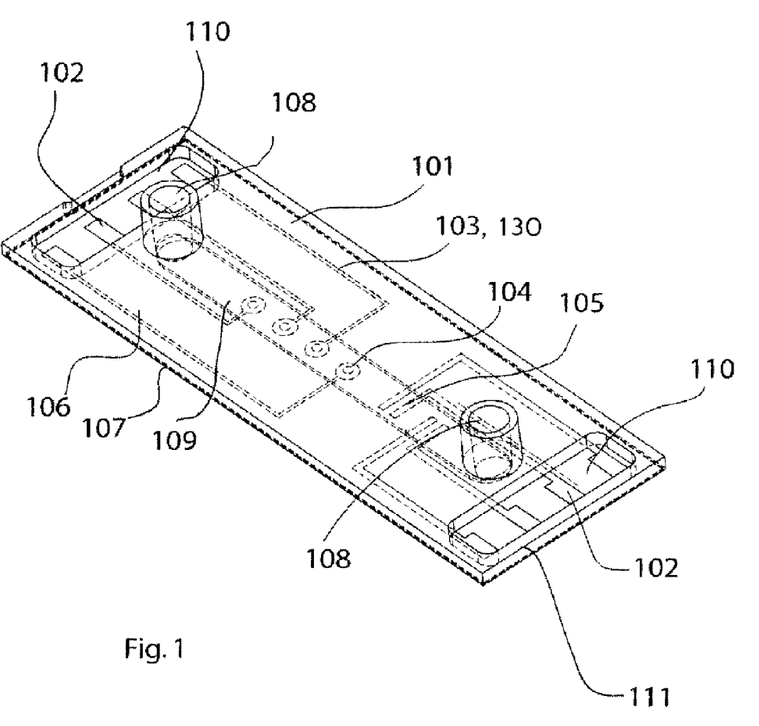
FIG. 1 shows a wire lattice drawing of an exemplary sample chamber.

FIG. 1 shows an example of a sample chamber 101, comprising contact electrodes 102, conductor elements and excitation and measuring electrodes 104, 105. In this embodiment the conductor elements are designed as conductor paths 103. Alternatively, semiconductor elements 130 may be provided. The sample chamber is, in this embodiment, rectangular. The planar part of the sample chamber may have a size, for example, of 75 mm ×25 mm ×2 mm. Four contact electrodes 102 are respectively located at the bottom of each one of the two blind holes 110. The two blind holes 110 are arranged on the opposite ends of the longitudinal axis of the sample chamber 101. One contact electrode 102 is connected by one conductor path 103 to one measuring electrode 104 or excitation electrode 105. The excitation electrodes 105 and the measuring electrodes 104, respectively, are arranged in a sample reservoir which is designed as a channel-shaped hollow space 109. Parts of the cover plate 106 are designed as an outwardly open, further reservoir 108. The two further, outwardly open reservoirs 108 are disposed on two opposite sides of the sample reservoir in the form of a channel-shaped hollow space 109. The cover plate 106 may be formed of an injection-molded part or may be formed by joining a plurality of plastic components.

Also, the contact electrodes 102 could each be arranged in a hole, whereby each hole could be a through-hole or a blind hole. Specifically, the contact electrodes may be arranged on the bottom and/or on a side wall of the hole. The contact electrodes 102 may be arranged in the bottom plate 107 or the cover plate 106, specifically entirely or partially in the hole. Thus, the contact electrode is directly accessible from the outside and an electrical contact with the contact electrode can be established. Especially if one contact electrode 102 is arranged in a hole, the hole may also be completely filled with a conductive material.

By means of the excitation electrodes 105, for example, defined currents or voltages at predetermined frequencies may be applied. Also, it is possible to control the temperature of the sample chamber 101 by a defined current flow through the electrodes. Specifically, corresponding arrangements of the conductor paths 103 or semiconductor elements may be used to control the temperature of the sample chamber 101. Specifically, ITO may be used for this application.

Depending on their design, the measuring electrodes 104 can receive electric signals so as to determine voltages, currents or also temperatures.

The sample chamber 101 may be substantially comprised of a cover plate 106 and a bottom plate 107, whereby the cover plate 106 may include a recess or groove or a hole, respectively. The bottom plate 107 may be formed of a planar surface, e.g. a glass carrier or a plastic sheet. The recess or groove on the inner side of the sample chamber defines a sample reservoir in the form of a channel-shaped hollow space 109.

In this embodiment the excitation electrodes 105 and the measuring electrodes 104 are located on the bottom of the sample reservoir in the form of a channel-shaped hollow space 109 which can be filled via the further, outwardly open reservoirs 108 fluidically connected to the same. The excitation and measuring electrodes 105, 104 may also be arranged on the bottom of an outwardly open sample reservoir.

In the example shown herein, contact electrodes 102, measuring electrodes 104, excitation electrodes 105 and conductor paths 103 are arranged on the bottom plate 107, with the contact electrodes 102 being located on the bottom of a blind hole 110. If the bottom plate 107 and the cover plate 106 are connected to each other, specifically surface to surface, the contact electrodes 102 are fixed in position because the cover plate 106, e.g. in the form of a "web" 111, provides for a corresponding stability. If the bottom plate 107 with the contact electrodes 102 would project over the edge of the cover plate 106, this part of the bottom plate 107 would easily break off, especially if normal cover glass (thickness of 170 μm) or a plastic sheet (thickness between 100 and 200 μm) is used. Also, bending it correspondingly relative to the cover plate 106 could cause cracks in the conductor paths 103.

The measuring electrodes 104 and the excitation electrodes 105 are here located on the bottom plate 107. However, also arrangements are possible where the measuring electrodes 104 and/or the excitation electrodes 105 are located on the cover plate 106 or on the bottom plate 107 and the cover plate 106. By connecting the bottom plate 107 and the cover plate 106 an electrical contact can, in the latter case, be realized between the contact electrodes 102 arranged, for example, on the bottom plate 107 and the measuring electrodes 104 arranged, for example, on the cover plate 106. In this case, joining techniques without the use of adhesives are advantageous (for example, welding techniques).

The electrodes and/or conductor paths 103 may specifically be vapor-deposited or printed conductive layers of gold, platinum, titanium etc., which have layer thicknesses of 10 nm to 5 μm. By connecting the cover plate 106 and the bottom plate 107 parts of the conductor path 103, which are located in the connection area of the bottom plate 107 and the cover plate 106, are completely insulated. If the use of only small electrodes as measuring electrodes 104 is desired, the corresponding measuring electrodes 104 in an outwardly open sample reservoir and/or in the sample reservoir in the form of a channel-shaped hollow space 109 may be coated with an insulating layer. This layer may extend only over the relevant portion of the sample reservoir or over the entire conductor path 103. The connection of the cover plate 106 to the bottom plate 107 may be accomplished by gluing or welding. Especially in the case of non-insulated conductor paths 103 thermal welding or solvent welding has proved to be effective.

The sample chamber may comprise, for example, features as described in DE 101 48 210.

Figure 2:
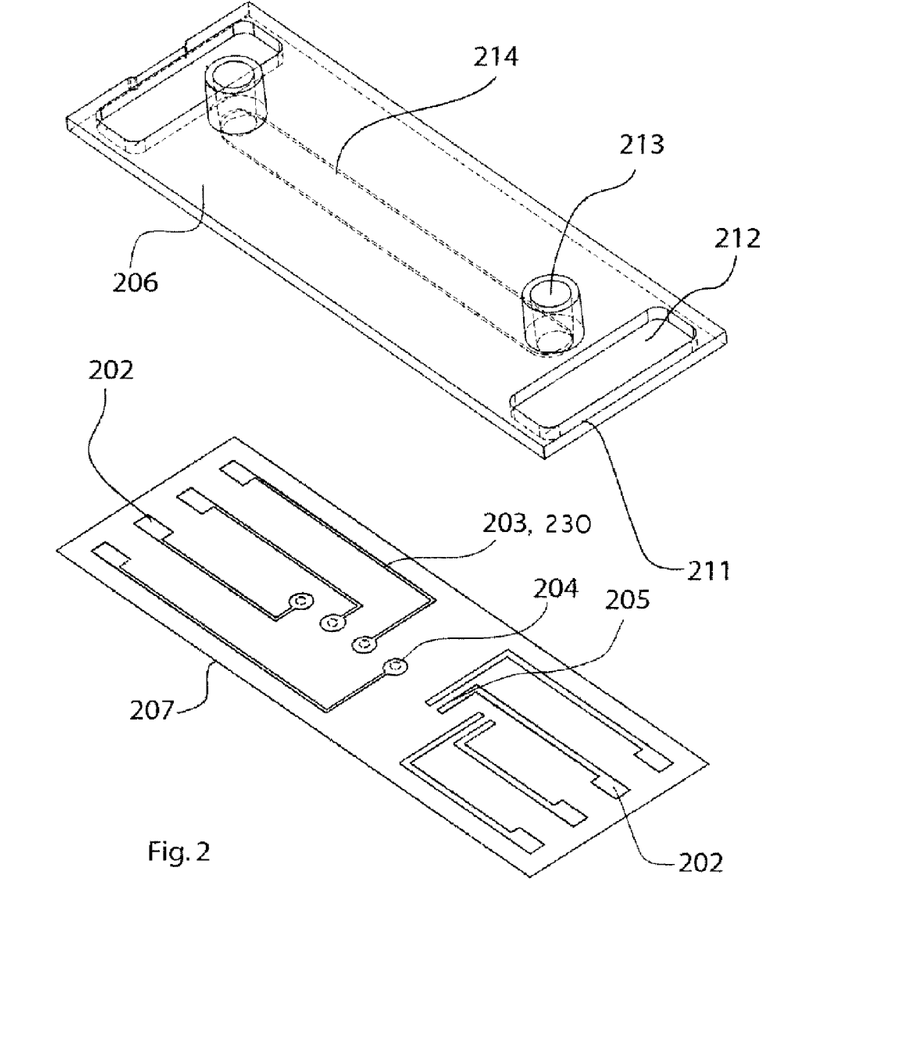
FIG. 2 shows an exploded view of the exemplary sample chamber of FIG. 1.

FIG. 2 shows an exploded view of the exemplary sample chamber of FIG. 1. Holes 212 and 213 are provided in the cover plate 206. Conductor paths 203 or semiconductor elements 230 are provided on the bottom plate 207. These conductor paths 203 may be realized as non-insulated or partially insulated conductor paths 203. One contact electrode is electrically conductively connected by one conductor path 203 to one measuring electrode 204 or excitation electrode 205, respectively. A groove 214 is provided in the cover plate 206, which defines in connection with the bottom plate 207 a sample reservoir in the sample chamber, the sample reservoir being in the form of a hollow space and provided between the cover plate 206 and the bottom plate 207. In the cover plate 206 a through-hole 213 is provided to define in the sample chamber the orifice of a further, outwardly open reservoir.

Figure 3:
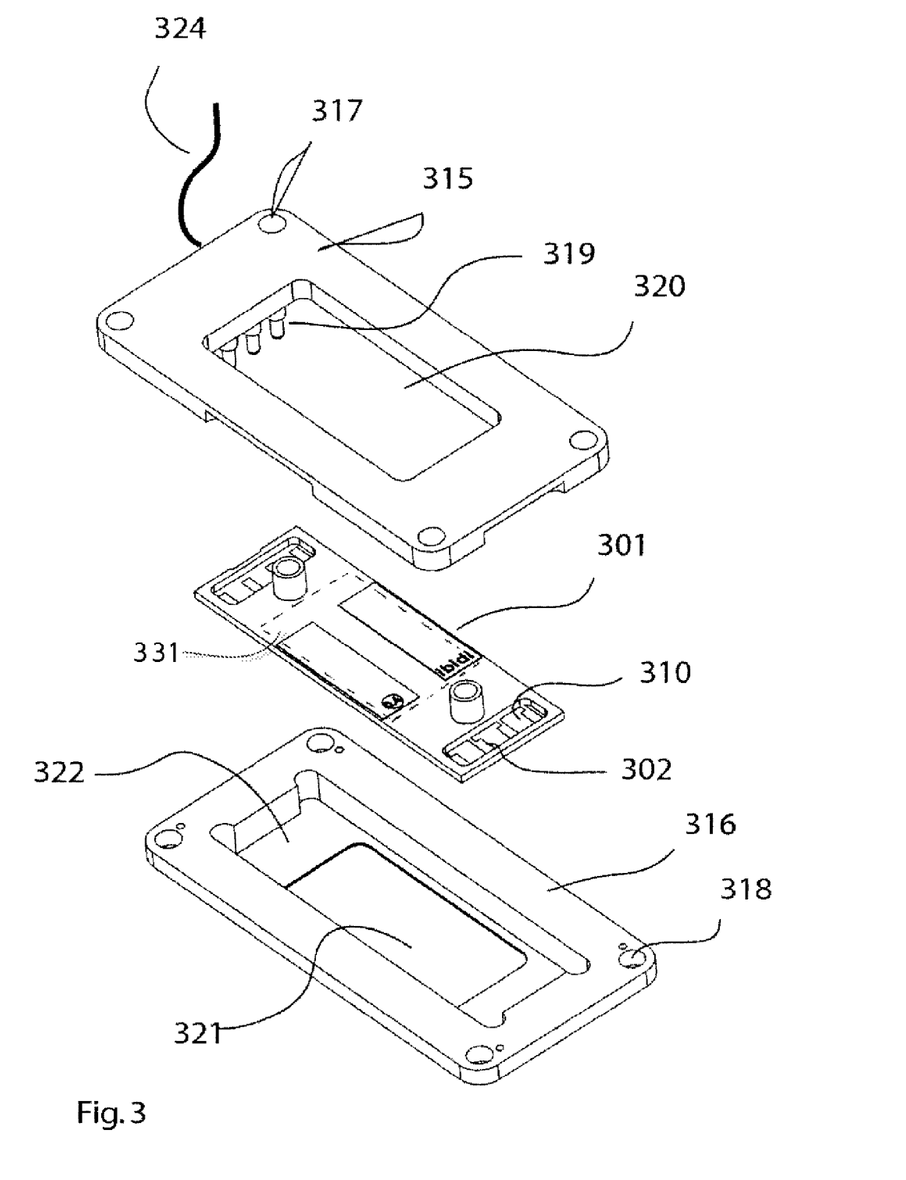
FIG. 3 shows a perspective view of an exemplary system comprising a sample chamber and a sample chamber holder.

FIG. 3 shows a perspective view of an exemplary system comprising a sample chamber 301 and a sample chamber holder. The sample chamber holder comprises a first frame element 315 and a second frame element 316. In this embodiment the frame elements are held together by the force of the incorporated magnets 317, 318 when the first frame element 315 and the second frame element 316 are placed on one another. Four magnets respectively are provided in the first frame element 315 and in the second frame element 316. One magnet respectively is disposed per corner of the rectangular frame elements. The magnets have to be strong enough to press a contact element 319, specifically a spring contact, firmly onto the contact electrode 302 of the sample chamber 301. Cylindrical permanent magnets 317, 318 having a diameter of 5 mm and a height of 4 mm may be employed, which can specifically be arranged in such a way that, in the assembled sample chamber holder, the magnets have a distance not exceeding 2 mm. The magnets may thereby have such a strength that a planar plate of COC, which has a thickness of 2 mm, which is fixed in the sample chamber holder and which has a slight curvature of 50 μm over 75 mm, is pressed to become even.

Thus, the force is sufficient to connect the contact element 319 of the sample chamber holder, specifically a spring contact, firmly to the contact electrode 302 of the sample chamber. Thus, the two frame elements of the sample chamber holder need not be screwed together, and the sample chamber holder may be realized so compact and miniaturized to allow its integration in an incubation apparatus.

In the embodiment shown several contact elements 319, specifically contacting pins or spring contacts, are incorporated in the first frame element 315. In the second frame element 316 of the sample chamber holder a corresponding recess 322 is provided for placing the sample chamber 301 therein. Preferably, the areas 320 and 321 are open. Thus, the sample in the sample chamber 301 can be viewed without problems. The areas 320 and 321 may also be covered, however. Thus, area 321 and/or 320 could be covered, for example, with transparent glass or plastic. Specifically, the glass or the plastic may be temperature-controllable (e.g. by an ITO coating). Again, the temperature of the entire sample chamber holder itself may be controllable. All electrical elements and/or contacts in the sample chamber holder can be triggered by a cable 324.

In order to control the temperature of the entire sample chamber holder passively, the sample chamber holder may be placed into a correspondingly temperature-controllable plate. This plate may be designed to fit into the standard microscope holder for a 96-well plate. Instead of the cable 324, which leads out of the sample chamber holder into the corresponding (electric/electronic) appliances, also a direct plug connection between the sample chamber holder and the plate may be provided. In this case, the connecting cable could, again, be directly connected to the plate in which corresponding connections are incorporated.

Alternatively or additionally, the sample chamber 301 may comprise a heating element 331.

In the sample chamber 301 a blind hole 310 is provided in which the contact electrodes 302 are located. If the sample chamber 301 is located in the assembled sample chamber holder, the contact elements, specifically spring contacts 319, press onto the contact electrodes 302. A firm contact is achieved by the magnets 317, 318 disposed in the first and second frame element, so that the contact elements 319 are pressed onto the contact electrodes 302 in the assembled sample chamber holder.

Figure 4:
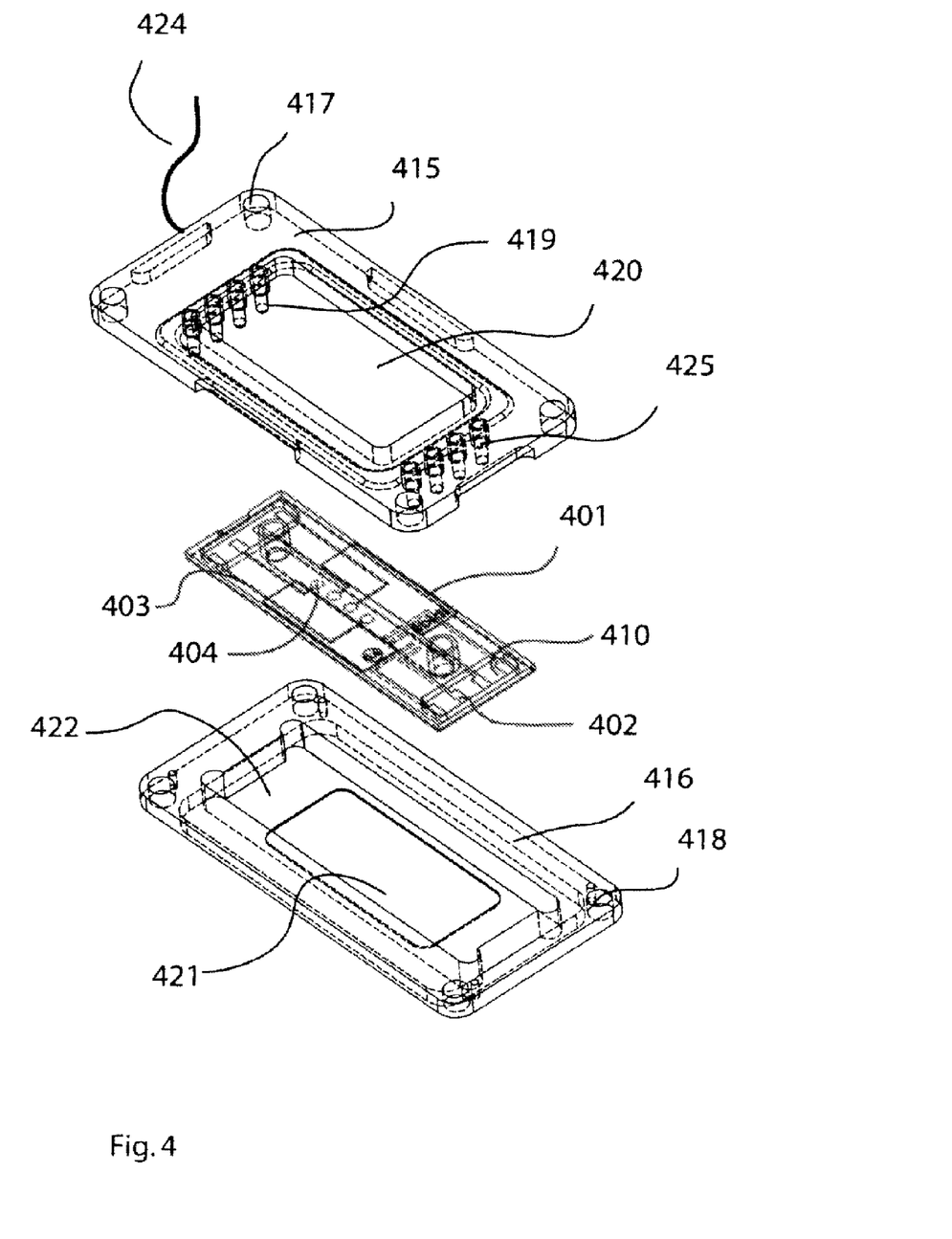
FIG. 4 shows a wire lattice drawing of the system of FIG. 3.

FIG. 4 shows an exemplary system comprising a sample chamber 401 and a sample chamber holder of FIG. 3 in a wire lattice drawing. Thus, in addition to all of the features shown in FIG. 3, also further contact elements 425 of the sample chamber holder become recognizable. Equally visible are, beside the contact electrodes 402, the conductor elements which are realized as conductor paths 403 and lead to the excitation or measuring electrodes 404. By means of a cable 424, which is only schematically shown, all electrical elements and/or contacts in the sample chamber holder may be contacted.

Figure 5:
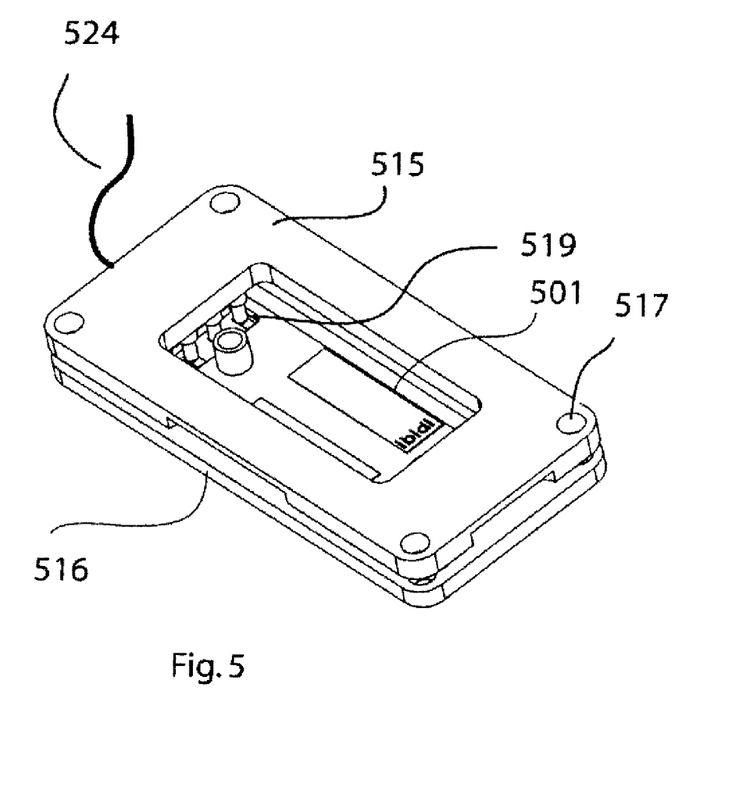
FIG. 5 shows a perspective view of the assembled system of FIG. 3.

FIG. 5 shows a perspective view of the assembled, exemplary system of FIG. 3. The frame elements 515, 516 are held together in a predetermined relative position by magnets 517. The contact elements 519 of the sample chamber holder are directly connected to the contact electrodes of the fixed sample chamber 501. The fixed sample chamber 501 is accessible from the outside through an open area in the first frame element 515. Specifically, orifice 513 in the cover plate of the sample chamber 501 is accessible, through which the further, outwardly open reservoir of the sample chamber 501 can be filled or emptied, respectively.

A sample chamber as is shown in FIG. 1 can be produced, for example, in such a way that the cover plate is exposed to a solvent vapor (as swelling agent for the polymer) and is subsequently connected, specifically pressed, to the bottom plate on which, for example, the contact electrodes, the measuring or excitation electrodes and conductor paths are located.

Instead of or in addition to the conductor elements of the exemplary sample chamber of FIG. 1 a sample chamber may also comprise semiconductor elements. Specifically, semiconductor elements, e.g. ITO, may be used as heating elements.

The invention claimed is:

1. A system for testing samples, the system comprising:
    a sample chamber comprising:
        a bottom plate and a cover plate connected thereto,
        a sample reservoir for receiving a liquid and/or a sample to be tested, and
        a contact electrode which is arranged entirely in the bottom plate, in the cover plate or between the bottom plate and the cover plate and which is electrically conductively connected to a conductor element or semiconductor element disposed in and/or on the sample chamber,
    wherein the bottom plate and/or the cover plate are designed in such a way that an electrical contact with the contact electrode can be established from an outside in such a way that an electrically conductive connection to the conductor element or to the semiconductor element can be established from the outside through the bottom plate or through the cover plate via the contact electrode,
    a hole in which the contact electrode is arranged, wherein the hole is a blind hole and the contact electrode is arranged to underlie a bottom opening of the blind hole and/or on a side wall of the blind hole, and
    a measuring electrode and/or an excitation electrode each of which are electrically conductively connected to a contact electrode by a conductor element or a semiconductor element,
    wherein the conductor element and/or the semiconductor element are disposed between the bottom plate and the cover plate or entirely on an outer side of the sample chamber or partially between the bottom plate and the cover plate and partially on the outer side of the sample chamber; and a sample chamber holder comprising:

a first frame element and a second frame element, an electrical contact element disposed on the first frame element or the second frame element, and a connecting device adapted to connect the first frame element to the second frame element so as to construct an assembled sample chamber holder having predetermined relative positions of the frame elements with respect to each other, wherein the connecting device comprises at least one magnetic and/or magnetizable element, wherein the first frame element and the second frame element are adapted to fix the entire sample chamber in the assembled sample chamber holder between the first frame element and the second frame element, and wherein, in the assembled sample chamber holder, the electrical contact element of the sample chamber holder is adapted to be electrically conductively connected to the contact electrode of the fixed sample chamber.

2. The system according to claim 1, wherein the first frame element and/or the second frame element include recesses for receiving the sample chamber.

3. The system according to claim 1, wherein the electrical contact element of the sample chamber holder comprises a spring contact.

4. The system according to claim 1, wherein the first frame element and/or the second frame element are adapted to allow a microscopical examination of a sample in the sample chamber fixed in the sample chamber holder.

5. The system according to claim 1, wherein the first frame element and/or the second frame element include a through-hole or a transparent area in the area of the sample chamber fixed in the sample chamber holder.

6. The system according to claim 5, wherein the through-hole or transparent area is made of glass or plastic.

* * * * *